United States Patent [19]

Lazzara et al.

[11] Patent Number: 4,955,811
[45] Date of Patent: Sep. 11, 1990

[54] NON-ROTATIONAL SINGLE-TOOTH PROSTHODONTIC RESTORATION

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 210,421

[22] Filed: Jun. 23, 1988

[51] Int. Cl.$^5$ ............................................. A61C 8/00
[52] U.S. Cl. ...................................... 433/173; 433/213
[58] Field of Search ............ 433/173, 174, 175, 201.1, 433/213

[56] References Cited

U.S. PATENT DOCUMENTS

| | | | |
|---|---|---|---|
| 4,713,003 | 12/1987 | Symington et al. | 433/173 |
| 4,744,753 | 5/1988 | Ross | 433/173 |
| 4,758,161 | 7/1988 | Niznick | 433/173 |

*Primary Examiner*—John J. Wilson
*Attorney, Agent, or Firm*—Alfred H. Rosen

[57] ABSTRACT

A method and a system for preparing a single-tooth prosthodontic restoration for non-rotational fixation to a dental implant fixture of the kind having a threaded socket together with anti-rotation means to restrain components non-rotationally attached to the fixture. The system provides a set of attachments comprising a two part impression coping having anti-rotation means cooperative with the anti-rotation means of the fixture and index means to fix the coping against rotation when encased in resilient impression material, a laboratory analog having a replica of the anti-rotation means of the fixture and core means on which to fabricate the restoration, the core means having a replica of the anti-rotation means of the impression coping. The method of using the system prepares a single-tooth restoration for fixation on an implanted fixture non-rotationally and with the desired orientation around its axis, so that no stabilizing connection to an adjacent tooth is required.

15 Claims, 2 Drawing Sheets

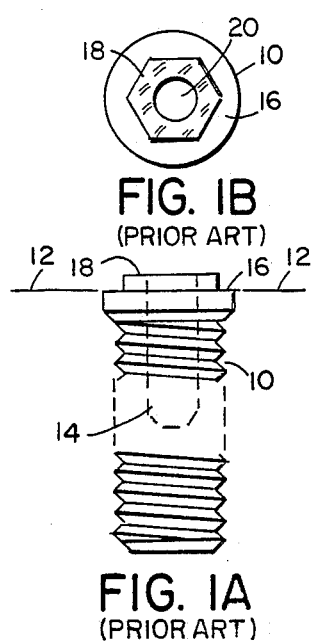
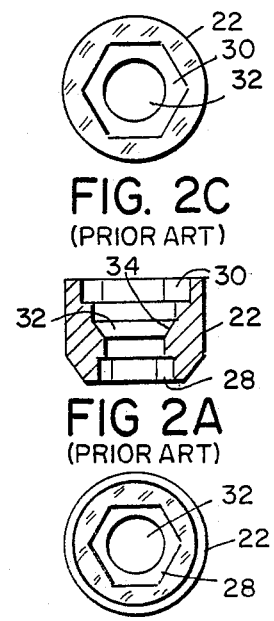
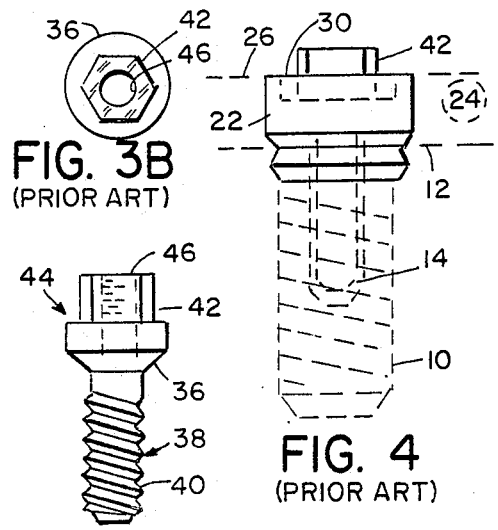
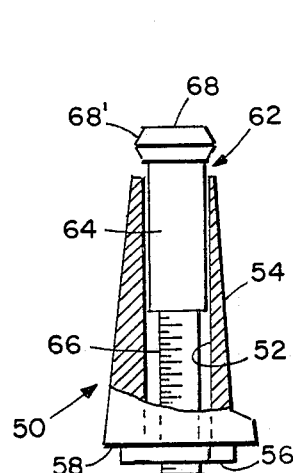
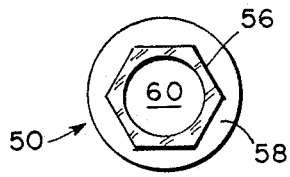
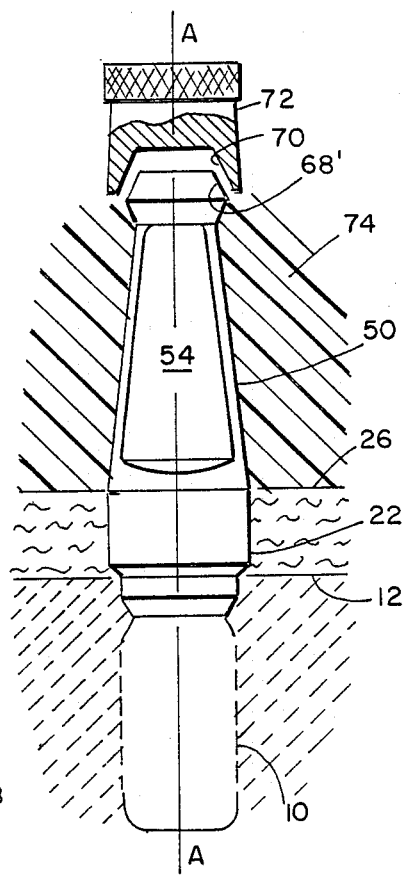
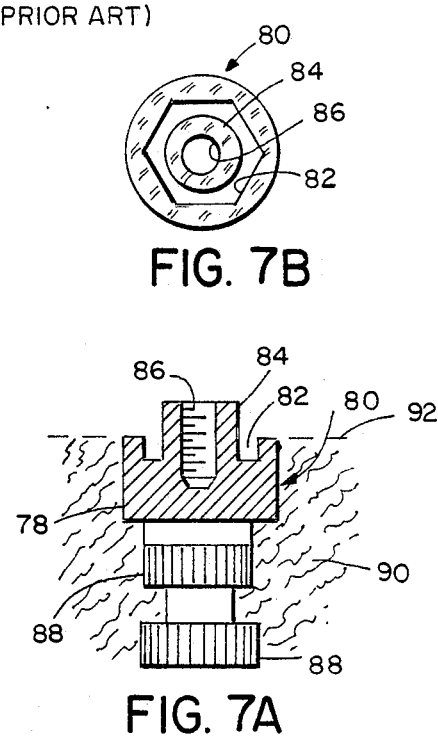
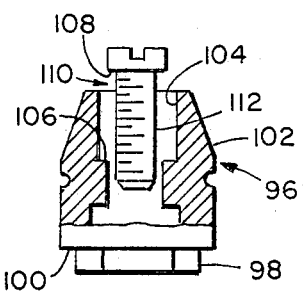

NON-ROTATIONAL SINGLE-TOOTH PROSTHODONTIC RESTORATION

BACKGROUND OF THE INVENTION

Single-tooth prosthodontic restorations present the unique requirement that they must be supported non-rotationally on the underlying abutment. When a prepared natural tooth is the underlying abutment this requirement is met in the normal course of preparing the abutment with a non-circular cross-section. Likewise, when the underlying abutment is a post fitted into a root canal this requirement is met by preparing the post with a noncircular cross-section. But, when the underlying abutment is itself supported on a dental implant fixture these options are not available to the prosthodontist. One technique that is available is to anchor the restoration to one or both of the adjacent natural teeth; however this technique requires that the adjacent tooth or teeth be prepared, as by grinding away some part of existing healthy enamel and dentin to accept a supporting fixture, which is undesirable.

A dental implant fixture is implanted into the bone of a patient's jaw and supports a socket which is accessible through the overlying gum tissue for receiving and supporting one or more attachments or components which in turn are useful to fabricate and to support the prosthodontic restoration. Dental implant fixtures can use a variety of implanting modalities; i.e.: blade, bone screw or smooth post, as examples. The present invention is not concerned with the implant modality that is used. The invention is concerned with the fact that the sockets of many of the most successful dental implant fixtures presently in use are cylindrical in shape; if the socket is internally threaded no other internal shape is possible. Such a socket, by itself, cannot provide non-rotational fixing of a single-tooth prosthodontic restoration to a dental implant fixture. To overcome that deficiency some of the dental implant fixtures that are now available include anti-rotation mean to restrain components attached to the fixture against rotation relative to the implant fixture around the longitudinal axis through the socket. A common example is a polygonal (e.g.: hexagonal) male projection or female indentation located on the gingival surface of the implant concentric with the opening into the socket.

GENERAL NATURE OF THE INVENTION

It is the principal object of the present invention to provide a system of components and a method for fabricating a single-tooth prosthodontic restoration which can be fixed non-rotationally on a dental implant fixture of the kind having a threaded socket together with anti-rotation means to restrain components non-rotationally attached to the fixture. To this end, the present invention provides a set of attachments comprising a two-part impression coping having at one end anti-rotation means cooperative with the anti-rotation means of the fixture upon attaching the coping end-wise to the gingival end of the fixture, so as to fix the coping against rotation around the axis of the socket relative to the fixture, the coping having also index means to fix the coping against rotation around that axis when encased in resilient impression material, a laboratory analog having at one end a replica of the anti-rotation means of the fixture and a body extending from that end including means to fix the analog in rigid dental model material, and core means on which to fabricate the restoration, the core means having at one end a replica of the anti-rotation mean of the impression coping.

In use the coping is fitted to the implant fixture and an impression is made in a usual resilient impression material. The impression is removed from the coping and the coping is separated from the implant fixture. The coping is attached to the laboratory analog and then the coping is put back into the impression. Owing to the index means of the coping the latter takes up its original orientation in the impression, and the anti-rotation means of the laboratory analog replicates the orientation of the anti-rotation means of the implant fixture around the axis of the socket. In this posture the laboratory analog is imbedded in a rigid model of the patient's case. Then the impression is removed from the coping and the coping is detached from the laboratory analog. The anti-rotation means of the laboratory analog now replicates in the rigid model the position and orientation of the anti-rotation means of the implant fixture in the patient's mouth. The core means is then attached to the laboratory model and, choosing any technique desired, the prosthodontist can fashion on it a model of the restoration which, when completed, will include within it the core means or a replica of the core means. The finished restoration will in any case preserve the anti-rotation means of the core means so that when the restoration is fitted to the implant fixture it will be non-rotationally attached and, moreover it will have the correct orientation with respect to the adjacent teeth and it will not require attachment to any of them.

The set of components or attachments of the invention are novel individually as well as in a cooperative set, and they cooperate uniquely to provide new means and method for fabricating a single-tooth prosthodontic restoration which can be fixed non-rotationally on a dental implant fixture in a straightforward and reliable manner, not requiring any special measures to be taken to achieve a restoration of a single tooth which can stand alone in the same manner as a natural tooth. Such a restoration can be placed in the anterior arch without giving evidence that it is a restoration, a consideration of immense importance to many patients.

DETAILED DESCRIPTION OF ILLUSTRATIVE EMBODIMENTS

Illustrative embodiments of the invention are shown in the accompanying drawings, in which FIGS. 1 to 4 inclusive show an existing dental implant system with which the invention is useful;

FIG. 5 illustrates partially in longitudinal section a coping according to the invention;

FIG. 6 shows the coping of FIG. 5 attached to the implant system as shown in FIG. 4;

FIG. 6A is a section on line B—B of FIG. 6;

FIG. 7 shows a laboratory analog according to the invention;

FIG. 8 illustrates partly in longitudinal section a core component according to the invention;

Figure 9:
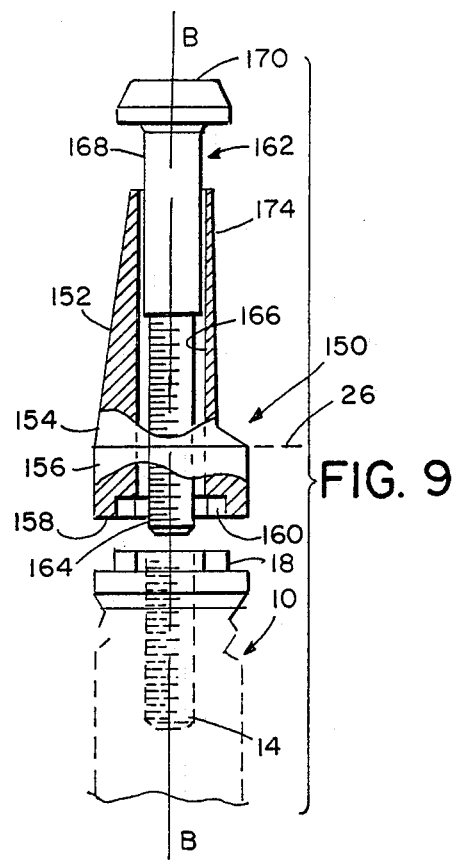
FIG. 9 illustrates partly in longitudinal section another coping according to the invention.

The components of FIGS. 5-8, inclusive, are used as a set, comprising a first embodiment of the invention; the components of FIGS. 9-12, inclusive, are used as another set, comprising a second embodiment of the invention.

Referring first to FIGS. 1-4, inclusive, a dental implant fixture 10, of the type intended to be screw-fitted in a hole surgically prepared in the patient's jawbone (not shown), the upper, or gingival, surface of which is represented by a dashed line 12, has an internally-threaded socket 14 opening to its gingival surface 16, on which a male annular fitting 18 having a non-circular (hexagonal) outer periphery is fixed, surrounding the opening 20 into the socket. FIG. 1A is a side view of this fixture; FIG. 1B is a view looking at the gingival surface 16. This fixture 10 is in common use for dental implantology, and it is available from several manufacturing sources. In use, after the implant fixture 10 has osseointegrated with the host bone, a transmucosal component 22 (FIG. 2) is fitted to the fixture, through an opening in the overlying gum tissue 24 (FIG. 4). Referring to FIG. 4, the surface of the gum tissue 24 is represented by a dashed line 26, and the transmucosal component 22 has a thickness approximating the thickness of the gum tissue. FIG. 2A shows the transmucosal component in longitudinal section; FIG. 2B is a bottom plan view of it; and FIG. 2C is a top plan view of it. Referring to FIG. 2B, this component has a first female hexagonal socket 28 sized to mate with the male hexagonal fitting 18. At the opposite end seen in the top plan view 2C this component has a second female hexagonal socket 30. A bore 32 passes completely through the transmucosal component 22 between the two female hexagonal sockets, and opens centrally through each of these sockets. This bore has, about midway between its openings, a tapered shoulder 34 for receiving a tapered boss 36 of a special assembly bolt 38, shown in FIG. 3.

The bolt 38 has an externally threaded shaft 40 intended to mate with the internally-threaded socket 14 in the implant fixture 10. When the transmucosal component 22 is fitted to the gingival surface 16 with the first female socket 28 embracing the male hexagonal fitting 18, the bolt 38 is screwed into the socket 14 until the tapered boss 36 is tight on the tapered shoulder 34, and the transmucosal component 22 is assembled non-rotationally to the implant fixture 10, as is shown in FIG. 4. The bolt 38 has a male hexagonal fitting 42 at its supragingival end 44, and a secondary internally threaded bore 46 opening through the end 44 coaxial with and extending toward the shaft 40. The hexagonal fitting 42 of the bolt 38 occupies the central volume within the second female hexagonal socket 30, leaving an annular volume that is accessible to other components, as is shown in FIG. 4. This hexagonal fitting 42 is used to tighten the bolt 38 on the implant fixture 10. The present invention, as illustrated in FIGS. 5-8, inclusive, makes use of the second female hexagonal socket 30 (hereinafter referred to as "hex-socket 30") and the secondary internally-threaded bore 46 (hereinafter referred to as "receiving bore 46").

Referring now to FIGS. 5 and 6, the coping 50 is an elongated generally cone-shaped body having a bore 52 passing axially through it and, to one side of this bore, a flattened outer surface portion 54 (hereinafter the "flat surface 54"). At its wider, lower end the coping 50 has a male hexagonal fitting 56 fixed on its lower surface 58 annularly embracing one opening 60 into the bore 52. This male hexagonal fitting 56 is sized to fit snugly within the hex socket 30. A coping bolt 62 has a principal shaft section 64, the diameter of which is only slightly smaller than the internal diameter of the bore 52. A threaded bolt section 66 of smaller diameter sized to thread into the receiving bore 46 extends from one end of the principal shaft section. A manipulating head 68 at the other end of the principal shaft section manipulating head is symmetrical around the longitudinal axis of the bolt. A conically-tapered outer surface 68' is provided for frictional engagement in a conical socket 70 of a driver 72, shown in FIG. 6.

In use, the coping 50 is attached to the transmucosal component of the existing implant system by engaging the bolt 62 in the receiving bore 46 and tightening the head 68 on the top end of the coping, using the friction driver 72. The coping is then non-rotationally attached to the implant fixture 10 and the flat surface 54 has a unique orientation around the axis A—A of the system, relative to the implant fixture. The manipulating head, being symmetrical around that axis, has no such unique orientation. An impression of the coping taken in a usual resilient impression material, indicated at 74, will make a record of the unique orientation of the coping, in addition to all the other information for which dental impressions are made. This impression is made to the surface 26 of the gum tissue. The manipulating head 68 is generally bulbous and larger in diameter than the adjacent narrow end of the coping, and so serves to retain the coping in the impression material 74. The impression has a flat side 73 corresponding to the flat surface 54, shown in FIG. 6A.

After the impression is made, it is removed from the coping, and the coping is removed from the implant system 10-22 by unscrewing the bolt 62 from the receiving bore 46. The coping is then attached to the laboratory analog 80, shown in FIG. 7, using the bolt 62. The laboratory analog has at one end a female hexagonal socket 82 which replicates the hex socket 30 and extending centrally from this socket a post 84 which occupies the same position relative to the socket 82 as the bolt fitting 42 relative to the hex socket. The post 84, however, is axially symmetrical. A threaded bore 86 opening through the post 84 axially into the laboratory analog replicates the receiving bore 46. The laboratory analog has at its other end splined flanges 88 for fixing the analog 84 in rigid modelling material 90. In use the laboratory analog 80 is fixed in the modelling material with its main body 78 within the surface 92 of the model, so as to reproduce the posture of the transmucosal component 22 relative to the surface 26 of the gum tissue 24. This is accomplished by reinstalling the coping 50 in the impression 74, with the laboratory analog 84 attached to it and the flat side 73 lined up with the flat surface 54, and forming the rigid model with rigid impression material brought directly to the available surface of the resilient impression material 74.

After the rigid model has formed, the resilient impression is removed from the coping and the coping is detached from the laboratory analog. The female hexagonal socket 82 now has exactly the same posture in the resulting model as the hex socket 30 has in the patient's jaw, owing to the memory function of the flat surface 54. The model is now ready to receive a core component capable of preserving this orientation memory, on which to fabricate a prosthodontic restoration. A suitable core component 96 is shown in FIG. 8. This core component has at one end (the lower end as shown in the figure) a male hexagonal fitting 98, fixed on its lower flat surface 100, which replicates the male hexagonal fitting 56 of the coping 50. Above this lower end the core component extends to a short tapered body 102 the side walls of which may have flattened portions or other means to restrain a prosthodontic restoration (not shown) from rotating around it when the core component is embraced in the restoration. A bore 104 runs axially entirely through the core component. An annular shelf 106, located about midway along the bore serves to stop the head 108 of a bolt 110, the threaded shaft 112 of which is dimensioned to thread into the receiving bore 86 in the laboratory analog 80.

In use, the core component 96 is attached to the laboratory analog in the rigid model, and a prosthodontic restoration (not shown) is fashioned on the model with the aid of the core component. The resulting restoration will preserve the axial orientation memory information originally provided by the coping 50. Upon removal from the rigid model, such a restoration can be installed on the implant system 10-22 in the patient's mouth and it will be fixed anti-rotationally in the patient's mouth flush with the surface 26 of the gum tissue 24, and with the desired orientation relative to adjacent teeth, without requiring any other means to restrain it from rotation around its axis.

The second embodiment of the invention uses components shown in FIGS. 9–12, inclusive, which do not require the presence of the transmucosal component 22. In use, this embodiment allows the preparation of a prosthodontic restoration for attachment directly to the implant fixture 10. A coping 150 has a tapered main body 152 the wider end of which (lower end 154 in the drawing) merges into a transmucosal section 156 having in its bottom surface 158 a female hexagonal socket 160 sized to mate with the male hexagonal fitting 18 of the implant fixture 10. This coping is attached to the implant fixture with a bolt 162 having at one end a threaded shaft 164 sized to mate with the internally-threaded socket 14. The coping has a bore 166 of uniform internal diameter running axially through it, and the bolt has a main shaft 168 of slightly smaller diameter sized to fit within this bore. A manipulating head 170, similar to the bolt head 68 shown in FIG. 5 is fixed to the upper end of the main shaft. The threaded shaft 164, of smaller diameter, is fixed to the lower end of the main shaft. The bolt 162 is turned into the socket 14 of the implant fixture with the friction driver 72, shown in FIG. 6. The coping 150 has on its tapered section 152 a flattened surface portion 174 to provide memory or orientation around the axis B—B, like the flat surface 54.

In use, the coping 150 is attached directly to the implant fixture 10, with the transmucosal section 156 passing through the gum tissue (not shown). The bolt head 170 is tightened on the upper narrow end of the main body 152 with the socket 160 embracing the male hexagonal fitting 18. With the coping thus non-rotationally attached to the implant fixture, an impression of the coping and the axially-symmetrical bolt head is taken to the surface 26 of the gum tissue (not shown). The impression is then removed from the coping, and the coping is detached from the implant fixture, and transferred to the laboratory analog 180 of this set of components, shown in FIG. 10, using the bolt 162.

Figure 10B:
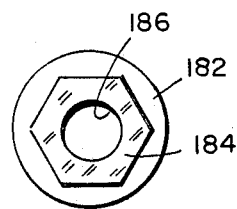
FIG. 10 shows another laboratory analog according to the invention.
Figure 10A:
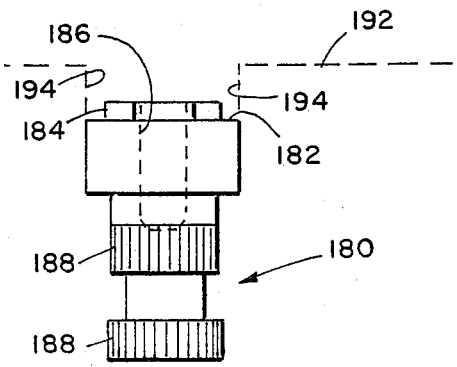

The laboratory analog 180 has on its upper surface 182 (as seen in FIG. 10) a male hexagonal fitting 184 which replicates the male hexagonal fitting 18 of the implant fixture 10. FIG. 10B is a plan view of the upper surface 182. Opening centrally through this fitting is an internally threaded socket 186 which replicates the socket 14 of the implant fixture. Thus, the upper surface 182, hexagonal fitting 184 and socket 186 of the laboratory analog 180 are replicas, respectively, of the upper surface 16, hexagonal fitting 18 and socket 14 of the implant fixture 10. The laboratory analog 180 has at its lower end splined flanges 188 for fixing the analog 180 in rigid modelling material 190, shown in FIG. 12.

Figure 12:
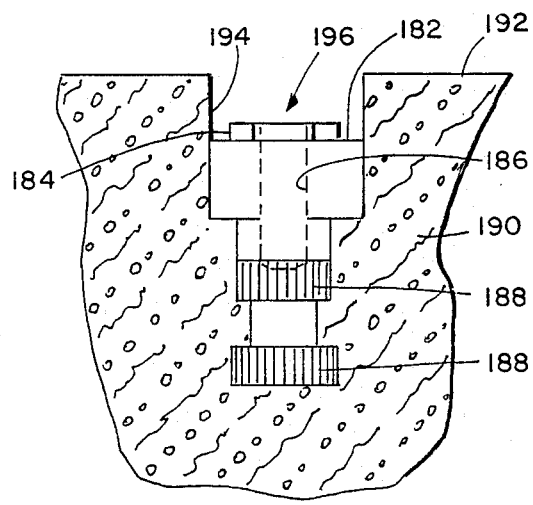
FIG. 12 illustrates a rigid model as made using the components of FIGS. 9 and 10.

The impression of the coping stops at the gum tissue surface 26, shown in FIG. 9, so that the transmucosal section 156 of the coping extends out of the impression. Thus, when the coping 150 is transferred to the laboratory analog, and the impression is re-fitted to the coping, the material used to make the rigid model 190 will extend beyond the upper surface 182 of the laboratory analog to a boundary 192 so as to envelop the transmucosal section 156 at sides 194 and meet the impression at the surface 26 which replicates the surface of the gum tissue. This situation is illustrated in FIG. 10 by the dashed lines 192, 194, a section 194 of which indicates the locus of the side of the transmucosal section 156. The rigid model thus made will have a hole 196 in it defined by the transmucosal section 156, as is shown in FIG. 12. When the impression and the coping are removed from the rigid model, the top surface 182, the male hexagonal fitting 184 and the socket 186 will be seen at the bottom of that hole.

Figure 11A:
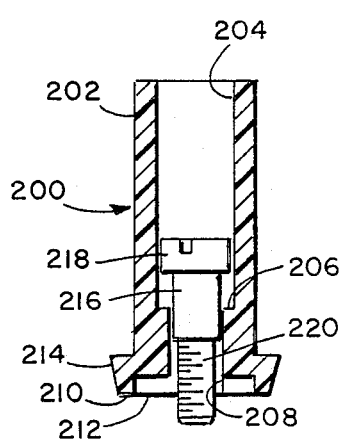
FIG. 11 illustrates in longitudinal section another core means component of the invention.

The core component 200 shown in FIGS. 11A and B is preferably made of a combustible plastics material. This component has a tubular main body 202 with a uniform internal bore 204. Near the lower end the bore 204 ends at an annular shoulder 206, and a narrower bore 208 extends between the shoulder and the bottom surface 210 through which the narrower bore opens centrally, as is best shown in the bottom plan view 11B. A female hexagonal socket 212 in the bottom surface 210 is sized to mate with the male hexagonal fitting 18 of the implant fixture 10, replicating the socket 160 in the coping 150. A flange 214 extending laterally from the outer sides of the main body 202 around its bottom end has approximately the same diameter as the transmucosal section 156 of the coping. This flange may have a slight taper for a snug fit in the hole 196 in the rigid model 190. A bolt having a main shaft section 216 with a diameter slightly smaller than the narrower bore 208, a head 218 sized to fit within the wider bore 204 and to rest on the shoulder 206 and, extending from the main shaft section a threaded shaft 220 of smaller diameter sized to mate with the socket 14 in the implant fixture 10 is used to attach the core component 200 to the laboratory analog 180 in the rigid model 190.

With the core component 200 attached to the model 190, a prosthodontic restoration can be fashioned to extend beneath the gum line, in which the non-rotational memory contributed by the coping is preserved. The tubular main body 202 can be cut to a desired length and the finished prosthesis can be attached to the implant fixture with a bolt, like the bolt 216-218-220, non-rotationally and in the correct orientation around the axis B—B. It will be fixed in the patient's mouth without requiring support from adjacent teeth, and its cosmetic material ca extend below the gum, like a natural tooth.

Figure 11B:
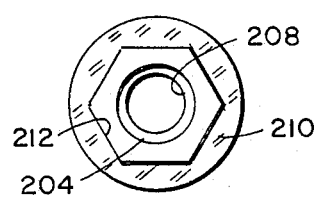

The flange 214 as illustrated in FIG. 11 may be as little as 1 mm. in axial length; alternatively this flange can be extended axially, up to the surface 26 of the overlying gum tissue, if it is desired to employ the flange 214 in the function of a trans-tissue section.

In the claims that follow the term "dental implant fixture" is intended to include, in one embodiment, the fixture 10 with the transmucosal component attached to it (as shown in FIG. 6), and in the other embodiment, the fixture 10 alone (as shown in FIG. 9), except where the claim is addressed specifically to only on embodiment of the invention.

We claim:

1. A set of attachments for use in fabricating a prosthodontic restoration intended to be fitted non-rotationally on a dental implant fixture having a threaded bore axially disposed in it and opening centrally through its gingival end, said fixture having at said gingival end anti-rotation means to fix said restoration when fitted against rotation relative to said fixture around a longitudinal axis running successively through said bore and said restoration, said set of attachments comprising an elongated impression coping having at a first one of its ends anti-rotation means cooperative with said anti-rotation means of said fixture upon attaching said coping end-wise to said gingival end of said fixture so as to fix said coping against rotation around said axis relative to said fixture, said coping having a smooth bore extending through it from said first one of its ends to the second one of its ends concentric with and embracing said axis for passage of a bolt useful to attach said coping to said fixture via said threaded bore, said coping having index means to fix said coping against rotation around said axis when encased in resilient impression material, a laboratory analog of said fixture having at one end a replica of said anti-rotation means of said fixture and a body extending from said one end including means to fix said analog in a rigid dental model, and core means on which to fabricate said restoration, said core means having at one end a replica of said anti-rotation means of said impression coping, and extending between its ends a bore for passage of a bolt useful to attach said core means to said fixture via said threaded bore.

2. A set of attachments according to claim 1 in which each of said anti-rotation means has a non-circular configuration around said bore in a plane transverse to said axis, the anti-rotation means of said fixture and said analog being either both male type or both female type fittings having said configuration, and the anti-rotation means of said coping and said core being both fittings of the other type having said configuration.

3. A set of attachments according to claim 2 in which the male-type fittings are regular polygons having sides substantially parallel to said axis, and the female-type fittings are sockets of similar polygonal cross-section for snugly receiving and enclosing said male-type fittings.

4. In a set of attachments according to claim 1 an impression coping having the shape of a regular cone extending from said one end tapering to a smaller cross-section at a second end, wherein said index means is a flat-surface on said cone extending between said ends in a plane substantially parallel to but displaced from said axis.

5. In combination with the impression coping according to claim 1 a bolt for attaching said coping to said fixture, said bolt having a shaft section dimensioned to fit substantially snugly in said bore, a threaded section extending from one end of said shaft section for engaging in said threaded bore of said fixture, and a head on the other end of said shaft section, said head being in close contact with said second end of said impression coping when said bolt is engaged in said threaded bore holding said impression coping fixed to said fixture, said head having a cross-section which is larger than the cross-section of said second end of said impression coping said head being smoothly contoured uniformly around said axis for engaging in said resilient impression material shape-wise uniformly around said axis.

6. In the combination according to claim 5 a bolt wherein said head has side walls tapering gradually downwardly to a smaller cross-section with respect to said axis, away from said shaft section.

7. In a set of attachments according to claim 1 core means comprising a base on which said anti-rotation means is formed and, extending from said base concentric around said axis a tubular member on which to fabricate said restoration, a shoulder within said tubular member near the junction of said base and said tubular member, for engaging the head of a threaded bolt when the latter is engaged in said threaded bore holding said core means fixed to said fixture.

8. Core means according to claim 7 wherein said tubular member is an elongated cylinder extending from said base member a distance greater than the supracoronal height of the prosthodontic restoration intended to be fabricated, said cylinder being made of a material that can be cut to a length desired for use in said restoration.

9. Core means according to claim 8 wherein said base has an axial length which is less than the thickness of the gum tissue surrounding said fixture, said base having a cross-section that is larger than the cross-section of said tubular member, providing an external annular shoulder for receiving the gingival aspect of said restoration.

10. Core means according to claim 7 wherein said base has an axial length which is approximately the same as the thickness of the gum tissue surrounding said fixture so as to function as a trans-tissue section.

11. A method of fabricating a prosthodontic restoration to be fitted non-rotationally on a dental implant fixture having a threaded bore axially disposed in and opening centrally through its gingival end, and having at its gingival end anti-rotation means to fix a prosthodontic restoration against rotation relative to said fixture around a longitudinal axis running successively through said bore and said restoration, said method comprising the steps of fitting non-rotationally to said fixture an impression coping having mating anti-rotative means and index means to fix said coping against rotation around said axis when encased in resilient impression material, forming an impression of said coping in said impression material, removing said coping from said impression and separating said coping from said fixture, fitting non-rotationally to said coping a laboratory analog having at one end a replica of said anti-rotation means of said fixture, reinstalling said coping in said impression with said analog fitted to it and forming a stone model around said analog, again removing said coping from said impression and separating said coping from said analog, non-rotatively attaching to said analog core means having a replica of said anti-rotative means of said impression coping on which to fabricate said restoration, fabricating said restoration on said core means, preserving said last-named anti-rotative means, and installing said restoration on said fixture mated with said non-rotative means of said fixture.

12. An intermediate component for use in fabricating a prosthodontic restoration intended to be fitted non-rotationally on a dental implant fixture having a threaded bore axially disposed in it and opening centrally through its gingival end, said fixture having at said gingival end anti-rotation means to fix said restoration when fitted against rotation relative to said fixture around a longitudinal axis running successively through said bore and said restoration, said component comprising an elongated impression coping having at a first one of its ends anti-rotation means cooperative with said anti-rotation means of said fixture upon attaching said coping end-wise to said gingival end of said fixture so as to fix said coping against rotation around said axis relative to said fixture, said coping having a smooth bore extending through it between said one end and a second end concentric with and embracing said axis, for passage of a bolt useful to attach said coping to said fixture via said threaded bore, said coping having index means to fix said coping against rotation around said axis when encased in resilient impression material.

13. A coping according to claim 12 having the shape of a cone extending along said axis from said one end tapering to a smaller cross-section at said second end, wherein said index means is a flat side surface on said cone extending between said ends on a plane substantially parallel to but displaced from said axis.

14. A coping according to claim 12 and further including a bolt having a smooth shaft section dimensioned to fit substantially snugly in said smooth bore, a threaded section extending from one end of said shaft section for engaging in said threaded bore, and a head on the other end of said shaft section, said head being substantially symmetrical around said axis when said smooth shaft section is in said smooth bore, said head being larger in size transverse to said axis than the cross-section of said coping at said second end.

15. A coping according to claim 14 wherein said head has side walls tapering gradually from a larger transverse section nearer to said smooth shaft section to a smaller transverse section more remote from said smooth shaft section.

* * * * *